United States Patent [19]

Rosser et al.

[11] Patent Number: 4,567,301

[45] Date of Patent: Jan. 28, 1986

[54] PERFLUORO (IMIDOYLAMIDINE) DIAMIDINES

[75] Inventors: Robert W. Rosser; Timothy S. Chen; Chung-Heng Cheng, all of San Jose, Calif.

[73] Assignee: The United States of America as represented by the Administrator, National Aeronautics and Space Administration, Washington, D.C.

[21] Appl. No.: 741,405

[22] Filed: Jun. 5, 1985

Related U.S. Application Data

[60] Continuation of Ser. No. 528,777, Sep. 2, 1983, abandoned, which is a division of Ser. No. 366,025, Apr. 6, 1982, Pat. No. 4,434,106.

[51] Int. Cl.[4] ............................................. C07C 123/00
[52] U.S. Cl. .................................................... 564/243
[58] Field of Search ......................................... 564/243

[56] References Cited

U.S. PATENT DOCUMENTS 3,489,727  1/1970  Dorfman et al. .................... 564/243

Primary Examiner—Natalie Trousof
Assistant Examiner—L. Hendriksen
Attorney, Agent, or Firm—Darrell G. Brekke; John R. Manning; Robert D. Marchant

[57] ABSTRACT

Perfluoroether triazine elastomers having improved properties are prepared from oligomeric imidoylamidines that have, in turn, been prepared by the process of (a) reacting a perfluorodinitrile with liquid ammonia to yield a perfluorodiamidine, (b) isolating the perfluorodiamidine, (c) reacting the isolated diamidine with a perfluorodinitrile to yield a perfluoro(imidoylamidine) dinitrile, and then repeating steps (a), (b), and (c) to sequentially grow an oligomer of desired molecular size. The isolated amidine and nitrile intermediates are also disclosed. The elastomers can be fashioned into seals, gaskets, sealing components and the like.

3 Claims, No Drawings

PERFLUORO (IMIDOYLAMIDINE) DIAMIDINES

STATUS OF THE APPLICATION

This application is a continuation of application Ser. No. 528,777, filed Sept. 2, 1983, which is a divisional application of application Ser. No. 366,025, filed Apr. 6, 1982, now U.S. Pat. No. 4,434,106.

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

TECHNICAL FIELD

This invention is in the field of perfluoroalkylether triazines and perfluoroalkyl triazines and elastomers made therefrom. More particularly, the invention relates to an improved process for preparing such materials.

BACKGROUND

The perfluorotriazine polymers to which the present invention relates are, as a general class, known materials. See U.S. Pat. No. 4,242,498 issued Dec. 20, 1980 to Rosser, et al. These materials are tough, heat and chemical-resistant elastomers. These advanced properties allow their advantageous use in extreme environments and applications—for example as fuel tank sealants, O-rings, wire enamels, pneumatic ducts and edge closeouts in aircraft.

U.S. Pat. No. 4,242,498 discloses a 4-step preparation procedure for these elastomers. This procedure consists of (1) forming a poly(imidoylamidine) by the reaction under reflux conditions of anhydrous ammonia with certain perfluorinated alkyl or alkylether dinitriles; (2) forming a linear polytriazine by cyclizing the imidoylamidine linkages by reaction with certain perfluorinated alkyl or alkylether acid anhydrides or halides; (3) extending the linear polytriazine chain by further refluxing in anhydrous ammonia; and (4) heating to cyclize the new imidoylamidine linkages and thereby crosslink the polymer.

While this earlier process and the products it produced were good useful advances, they did pose shortcomings. For one, with this process, it was difficult to control or reproduce the molecular size of the polymer product. Moreover, the resulting polymer at times manifested some degree of hydrolytic instability.

Other patents that are of general interest in showing various other similar procedures for producing triazine elastomers of the general type described above include:
U.S. Pat. No. 3,347,901 issued on Oct. 17, 1967 to Fritz, et al;
U.S. Pat. No. 3,250,808 issued on May 10, 1966 to Moore, et al;
U.S. Pat. No. 3,450,646 issued on June 17, 1969 to Annand, et al;
U.S. Pat. No. 3,531,496 issued on Sept. 29, 1970 to Annand, et al;
U.S. Pat. No. 3,637,630 issued on Jan. 25, 1972 to Dorfman, et al;
U.S. Pat. No. 4,234,715 issued on Nov. 18, 1980 to Rosser, et al;
U.S. Pat. No. 4,245,085 issued on Jan. 13, 1981 to Rosser, et al; and
U.S. Pat. No. 4,273,918 issued on June 16, 1981 to Rosser, et al.

STATEMENT OF THE INVENTION

It has now been found that more uniform and reproducible perfluoroalkylether and perfuoroalkyl triazine elastomers result when certain improvements are made to the arttaught preparation process.

The process of this invention is a multistep process in which first a perfluorodinitrile is reacted with liquid ammonia to give a perfluorodiamidine which is isolated. This material is then reacted with additional perfluorodinitrile to give a perfluoro(imidoylamidine)dinitrile. These two steps are then repeated, that is, this new dinitrile is then reacted with liquid ammonia to give the corresponding perfluoro(imidoylamidine)diamidine which is freed of ammonia and is in turn reacted with additional dinitrile (either the original dinitrile, another dinitrile, or the imidoylamidinedinitrile) in a stepwise growth. This two step sequence can be repeated until a linear oligomer having the molecular size desired is achieved. Then the linear oligomer is cyclized with a triazine cyclizing reagent, preferably with a perfluoroacid anhydride to give an oligomeric perfluoro(triazine)dinitrile prepolymer which can be crosslinked to give an elastomer by heating in the presence of ammonia.

Expressed most directly, in the process of the invention, the prior art's reaction of ammonia and a perfluorodinitrile to give a polymer is newly broken down into its individual reaction steps by adoption of particular reaction conditions. These steps are repeated sequentially until the desired size product is reproducibly achieved.

In addition to this process, with or without the final cyclizing and crosslinking steps, this invention also provides the perfluorodiamidines and the poly(imidoylamidine)dinitriles as new chemical compounds.

DETAILED DESCRIPTION OF THE INVENTION

The Reaction Sequence

In particular, this new process involves (A) reacting a perfluorodinitrile MC—(R$_f$)—CN, wherein R$_f$ is either a bivalent fluorocarbon radical of the formula 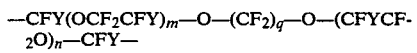—C$_p$F$_{2p}$—, wherein p is a number from 2 to 18 or a bivalent oligomeric oxyfluorocarbon radical of the formula —CFY(OCF$_2$CFY)$_m$—O—(CF$_2$)$_q$—O—(CFYCF$_2$O)$_n$—CFY— wherein Y is F or CF$_3$, q is a number from 1 to 18 and m and n are each numbers the sum of which is from 2 to 7, with a molar excess of liquid ammonia to form a perfluorodiamidine;

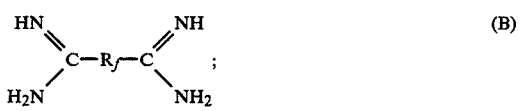

isolating the perfluorodiamidine; (C) reacting this isolated diamidine with additional perfluorodinitrile to produce an oligomeric (imidoylamidine)dinitrile

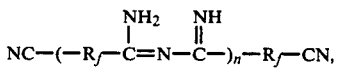

wherein n is a number initially 2, but ultimately from 2 to 50 inclusive, preferably 2 to 10 inclusive and more preferably 2 to 5. This (imidoylamidine)dinitrile is then (D) reacted as in step (A) with a molar excess of liquid ammonia to produce an (imidoylamidine)diamidine

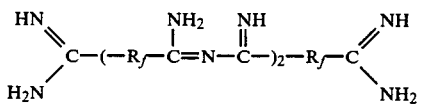

which is (E) isolated as in step (B) and (F) reacted with an appropriate dinitrile as in step (C). This growth is continued until the desired molecular size is attained at which time the nitrile is freed of unreacted ammonia and (G) reacted with a ring-closing reagent, especially a perfluorinated acid anhydride, $(R_f'CO)_2$—O, wherein $R_f'$ is a monovalent fluorocarbon radical or oxyfluorocarbon radical, to produce a perfluoro(triazine)dinitrile

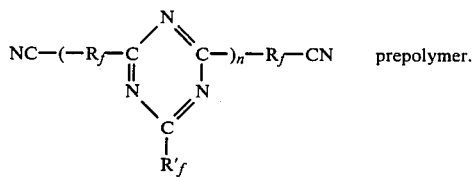   prepolymer.

Thereafter, this dinitrile prepolymer may be cured (cross-linked) to an elastomer by heating in the presence of added ammonia.

Feedstocks

The perfluorodinitrile feedstock, NC—($R_f$)—CN, may be selected from preferably linear but also branched fluorocarbon dinitriles, NC—$C_pF_{2p}$—CN, wherein p is a number from 2 to 18, preferably 5 to 12. These materials are known and may be prepared from the corresponding diacids which are marketed commercially by PCR Research Chemicals, Inc. The NC—(R$_f$)—CN feedstock may also be selected from oligomeric (perfluoroalkylether)dinitriles,

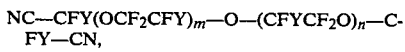

wherein Y is F or a trifluoromethyl group (—CF$_3$), q is a number from 1 to 18 inclusive (preferably 1–5, most preferably about 3), m and n are each numbers from 1 to 5 inclusive with the sum of m+n equal to 2 to 7. Preferably m and n are equal and are each 2 or 3. These materials are known and can be prepared as taught in U.S. Pat. No. 3,347,901 of Fritz, et al, which disclosure is incorporated herein by reference. Many of these materials are also available from PCR, Inc. $R_f$ represents the bivalent perfluorinated radicals which correspond to these dinitriles. Mixtures of two or more dinitriles may be used, as well.

The cyclizing agent feedstock is selected from the anhydrides, acyl halides (e.g. fluorides and chlorides) of perfluorinated lower (preferably branched, but also linear) aliphatic acids containing from 2 to 18 carbons and of the oligomeric perfluoroalkylether acids. These acids and their corresponding cyclizing agents are represented by the formulae

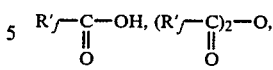

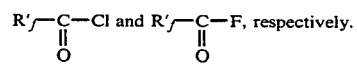

wherein $R_f'$ in a linear or branched 1 to 17 carbon (preferably branched 1 to 11 carbon) monovalent perfluoroalkyl radical of the formula —$C_rF_{2r+1}$, wherein r is from 1 to 17 (inclusive preferably 1 to 11) or an oligomeric perfluoroalkylether of the formula

wherein Y is F or a perfluoroalkyl group of 1 to 3 carbons especially F or CF$_3$, and y is an integer from 1 to 50 inclusive, preferably 1 to 10 and more preferably 1 to 5. Of these cyclizing reagents, the oligomeric perfluoroalkylether anhydrides, especially wherein Y is CF$_3$, and y is from about 1 to 3 inclusive are preferred. With these oligomeric materials, a mixture of chain lengths is often most easily obtained and may be used as may other mixtures. The perfluoro lower aliphatic acids are commercially available and their anhydrides and halides may be prepared by methods of the art. The perfluoroalkylether acids may be prepared by first making the corresponding acid fluorides according to the procedures of Moore et al's U.S. Pat. No. 3,250,808, by hydrolyzing to the free acids and then dehydrating such as with P$_2$O$_5$.

Reaction Conditions

The Diamidine Formation Reaction:

This reaction, whether carried out using the starting material dinitrile (i.e. Reaction A) or a dinitrile intermediate formed in the reaction sequence (i.e. Reaction D), is carried out in the presence of substantial excess liquid ammonia. Generally this is achieved by a slow, e.g. dropwise, addition of the dinitrile to the liquid ammonia with vigorous agitation. Preferably at least 10 and especially 15 to 200 equivalents of ammonia are present per equivalent of dinitrile. This reaction is carried out in liquid phase at temperatures at or below the boiling point of ammonia, generally at temperatures of from −60° to −33°, preferably −50° to −30°. If superatmospheric pressures are used to assure a liquid ammonia reaction phase, higher temperatures such as up to 50° C. can be used. The reaction times will vary between 0.1 and 24 hours, inversely depending upon the reaction temperature. Longer times may be used but are not required. If a solvent is present, such as a vehicle for the dinitrile, it should be a material that dissolves the reactants and is inert to them, with liquid flurorcarbons, especially the fluroocarbons marketed as FREON ®, and more especially FREON ® 113 (C$_2$Cl$_3$F$_3$) being preferred.

Isolation B:

This isolation step is employed to substantially free the amidine-forming reaction mixture of step A or of subsequent steps of ammonia and any added solvent. Preferably, the product of this isolation should contain as little ammonia as possible i.e. it should contain no more than 1% by weight of ammonia, more preferably less than 0.1% by weight NH₃. In view of the volatility of the solvent and NH₃, vacuum is a preferred method for their removal. Other equivalent means may be employed.

The Diamidine-Dinitrile Condensation C, etc.:

This reaction (reaction C, F, etc.) is carried out substantially in the absence of ammonia. One reactant is slowly admixed with the other at moderate temperature, in liquid phase generally in an inert reaction solvent. Preferred temperatures are from 0° C. to 70° C. with temperatures of from 5° C. to 60° C. being preferred. The reaction time ranges from 1 hour to 72 hours with, as a guideline, 24 to 48 hours being preferred at room temperature. The mole ratio of the two nitrile and amidine reactants is generally controlled at about 2.1 i.e. 1.5:1 to 2.5:1. Higher and lower ratios may be used as well but can lead to final products having differing properties. Also preferably, the amidine is added to the nitrile. The inert solvents discussed in step A may be suitably used in this step as well.

The Ring Closure G:

The reaction of the linear oligomeric dinitrile with the ring closing agent to yield an oligomeric prepolymer is carried out in the substantial absence of ammonia. Generally, an inert liquid reaction solvent is present, particularly the FREONs ® discussed in Step (A). A molar excess, i.e. greater than 1 and especially from 4 to 20 equivalents of ring closing agent is usually employed. Time and temperature for the reaction depend upon the type of ring closing agent employed. With anhydrides, moderate temperatures such as from 0° to 70° C. for 1 to 3 hours are usually adequate. With acid halides, stronger conditions are called for as from room temperature to 100° C. for 12 to 36 hours.

The Crosslinking Reaction:

Crosslinking is achieved by heating the oligomeric prepolymer with ammonia. Generally, a temperature of from 100° to 300° C. is employed for from 1 to 200 hours, especially 100° to 200° C. for from 12 to 100 hours. The amount of ammonia ranges from 0.1 to 4 equivalents per prepolymer molecule.

PRODUCTS

The linear oligomeric prepolymer material

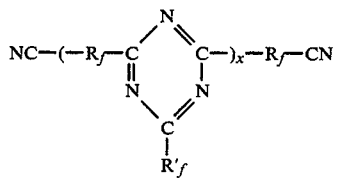

can range in molecular size from about 1500 daltons (when X equals 1 and $R_f$ and $R_f'$ equals the preferred perfluoro ethers) up to 10,000 daltons or higher such as up to 150,000 daltons. In other words X can range from 1 to 100, if desired. It has been found, however, that very excellent properties are imparted to the final elastomers when X is from about 3 to about 10, especially from 4 to 8 and most especially such as to give a molecular weight of 6000–6500.

The final crosslinked elastomers are characterized by uniform properties—especially uniform thermal, physical and chemical properties. They have a glass transition temperature of from −75° C. to −30° C. and exhibit less than 5% weight loss when heated in nitrogen or air for 3 days at 300° C. In addition, they resist hydrolytic attack. These final materials are excellent high performance elastomers and can be fabricated into a variety of seals, gaskets, sealing components and like by methods known in the art. Fillers and/or reinforcing agents can be added, if desired.

The invention will be further illustrated by the following Examples. They are presented to make clear the invention and are not to be construed as limiting its scope.

EXAMPLES

In these Examples, all temperatures are in °C., and all weights are in g unless otherwise noted. Infrared (IR) spectra were recorded on a Nicolet MX-1, FT-IR Spectrometer. Thermogravimetry measurements were recorded with DuPont Instruments, the 951 thermogravimetry analyzer and the 990 thermal analyzer. Glass transition temperatures (tg) were obtained with a DuPont differential scanning calorimetry (DSC) cell and 1090 thermal analyzer. Molecular weight values were determined by gel-permeation chromatography measurements using a Waters Associates ALC-GPC 202/401 liquid chromatograph equipped with a Spectra-Physics SP 4020 data interface and SP 4000 central processor/plotter. The SP system was programmed to correct for baseline and to compute the average molecular weight by comparison with known calibration points. Separations were observed by using DuPont size-exclusion (SE) columns having a Waters Associates differential UV detector at 254 mm or by a differential refractometer R 101 in FREON ® 113 solution according to the method of Korus and Rosser, *Anal. Chem.*, 50, 249 (1978). Gas chromatography results were obtained with a Hewlett-Packard Model 5830 gas chromatograph.

The 1,1,2-trichloro-1,2,2,-trifluoro ethane (FREON ® 113) was purchased from Fisher Scientific Company and distilled, using a 4-ft column of 6-mm procelain berl saddles at 48° C. Perfluoroalkylether dinitriles were purchased from PCR Inc., and hexafluoropropylene epoxide was obtained from E.I. DuPont de Nemours & Co. Other chemicals were either analtyical grade or better.

EXAMPLE 1

Ring Closing Agent Preparation: Preparation of Perfluoroalkylether Acid Fluoride and Its Corresponding Anhydride.

Mixed perfluoroalkylether acid fluorides (I) ($R_f'COF$) were prepared according to the procedure shown in U.S. Pat. No. 3,250,808 of Moore and Milian.

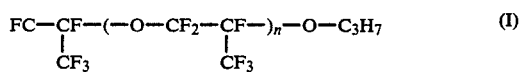

(n=1, 21%; 2, 72%; 3, 7%).

Hydrolysis of the acid fluoride mixture gave the corresponding perfluoroalkylether acids. The synthesis of the anhydrides of these perfluoroalkylether acids was performed by placing 200 g of the mixed perfluoroalkylether acids and 160 g of phosphorous pentoxide in a reaction flask; the mixture was heated to 180° C. and held at that temperature for 16 hr and then vacuum distilled. 150 g of the corresponding mixed perfluoroalkylether acid anhydride (II) was collected (85° C./16 mm Hg–120° C./0.5 mm Hg).

$$(R_f'CO)_2\text{—}O \tag{II}$$

The mixture was used without further purification.

Analytical data (IR liquid film): 1870,1805 cm$^{-1}$ (C=O), 1400-1050 cm$^{-1}$ (C—F).

A. Preparation of Perfluoroalkylether Diamidine

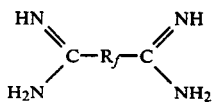

wherein $R_f$ represents

Twenty milliliters of NH$_3$ were condensed into a 100-ml, three-neck flask equipped with a dry-ice condensor, an NH$_3$ gas inlet, and an addition funnel. A solution of 10 g of perfluoroalkylether dinitrile NC—R$_f$—CN in 10 ml of FREON ® 113 was added dropwise into the flask with vigorous stirring.

B. After completion of the addition, excess ammonia and FREON ® 113 were removed by vacuum. Liquid perfluoroalkylether diamidine (10.5 g) III substantially free of ammonia was then collected without further purification.

Analytical data (IR liquid film): 3200-3000 cm$^{-1}$ (NH); 1684 cm$^{-1}$ (C=N); 1400-1050 cm$^{-1}$ (C—F).

C. Preparation of Perfluoroalkylether (Imidoylamidine)-Dinitrile (IV)

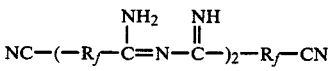

To a solution of 20 g of the perfluoroaklylether dinitrile NC—R$_f$—CN used in step A in 20 ml of FREON ® 113 the solution of 10 g of perfluoroalkylether diamidine (III) in 10 ml of FREON ® 113 was added dropwise with vigorous stirring for 2 hours at room temperature. After evaporating the solvent, 30 g of perfluoroalkylether (imidoylamidine)dinitrile (IV) was recovered as a viscous liquid.

Analytical data (IR liquid film): 3500, 3400, 3120 cm$^{-1}$ (N—H), 2260 (—C≡N), 1652, 1602, 1520 cm$^{-1}$ (imidoylamidine) 1400-1050 cm$^{-1}$ (C—F).

D. Preparation of Perfluoroalkylether (Imidoylamidine)-Diamidine (V)

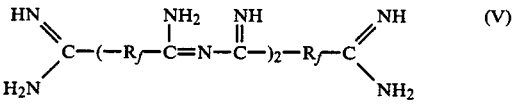

Perfluoroalkylether (imidoylamidine)dinitrile (IV) (30 g in 30 ml of FREON ® 113) was added dropwise to 30 ml of liquid ammonia with vigorous stirring for 3 hr at room temperature. Excess ammonia and solvent were then removed under vacuum and 30 g of perfluoroalkylether (imidoylamidine)diamidine (V) was obtained as a viscous liquid without further purification. This material could be reacted with a perfluorodinitrile such as (IV) or NC—R$_f$—CN or the like as shown to give a higher molecular weight dinitrile.

E. Preparation of Linear Perfluoroalkylether (Triazine) Dinitrile (VI) - Prepolymer

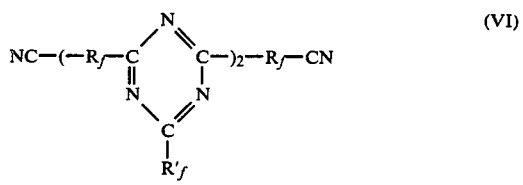

To 50 g of perfluoroalkylether acid anhydride (II) was added 25 g of perfluoroalkylether (imidoylamidine)dinitrile (IV) in 30 ml of FREON ® 113 with stirring for 2 hours. After removing the solvent, perfluoroalkylether acid, and excess perfluoroalkylether acid anhydride by vacuum distillation, 28 g of perfluoroalkylether (triazine) dinitrile (VI) prepolymer was obtained as a highly viscous liquid.

Analytical data (IR liquid film): 2260 cm$^{-1}$ —(—C≡); 1550 cm$^{-1}$ (triazine); 1400-1050 cm$^{-1}$ (C—F).

F. Preparation of Cross-Linked Perfluoroalkylether Triazine Elastomer

Thirty-five grams of a perfluoroalkylether (triazine) dinitrile having a (Mv 6200) were stirred with 1-2 equivalents of liquid ammonia and then heated in an open space in an over at 150° C. for 4 days to effect crosslinking. The resulting product (35 g) was a light tan perfluoroalkylether triazine elastomer with excellent properties. The glass transition temperature of the elastomer, determined by differential thermal analysis was about −45° C., and isothermal weight losses in air or nitrogen at 300° C. for 3 days were less than 5%.

Analytical data (IR liquid film): 1500 cm$^{-1}$ (C—F).

EXAMPLE 2

The preparation of Example 1 is repeated substituting perfluoromethylacetic acid anhydride as the triazine ring closure agent in step E. The resulting triazine prepolymer can be crosslinked to give an elastomer. This product is somewhat less hydrolytically stable than the product of Example 1.

EXAMPLE 3

The preparation of Example 1, parts A,B,C and D, is repeated. The diamidine (V) of part D (85g), as an ammonia-free liquid is dissolved in 10 ml of FREON 113 and added dropwise to a vigorously stirred solution of 10g of perfluoroalkylether (imidoylamidine)-dinitrile IV of part C of example 1. The mixture is stirred at room temperature for 2 hours. After evaporating the solvent, a high molecular weight perfluorodinitrile of the formula

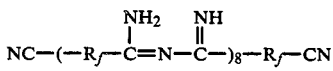

is recovered. This material is dissolved in 30 ml of Freon and then converted to a linear triazine prepolymer by the method of Example 1 part E, i.e. prepolymer by addition to 50g of anyhydride II, and stirring for two hours. This yields the triazine.

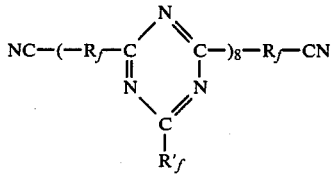

which can be cross-linked to give an elastomer in accord with Step F of Example I.

We claim:

1. A perfluoro(imidoylamidine)diamidine compound of the formula:

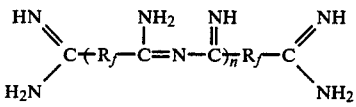

wherein n is a single number selected from 2 to 50 inclusive and wherein each $R_f$ is selected from perfluorocarbons of the formula $-C_pF_{2p}-$ wherein p is a number from 2 to 18 inclusive, and oligomeric perfluoralkylethers of the formula:

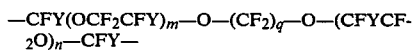

Y is F or $CF_3$, q is a number from 1 to 18 and m and n are each numbers, the sum of which is from 2 to 7.

2. The Perfluoro(imidoylamidine)diamidine of claim 1 wherein each $R_f$ is the same and n is 2 to 10.

3. The perfluoro(imidoylamidine)diamidine of claim 2 wherein n is 2.

* * * * *